United States Patent [19]

Duncan et al.

[11] 4,152,540
[45] May 1, 1979

[54] FEEDTHROUGH CONNECTOR FOR IMPLANTABLE CARDIAC PACER

[75] Inventors: Donald A. Duncan, Cambridge, Mass.; Lawrence E. Brown, New Kensington, Pa.

[73] Assignee: American Pacemaker Corporation, Woburn, Mass.

[21] Appl. No.: 793,393

[22] Filed: May 3, 1977

[51] Int. Cl.² .................. H01B 17/26; A61N 1/36
[52] U.S. Cl. ........................ 174/152 GM; 29/631; 128/419 P; 228/122; 228/208; 228/245; 361/302; 361/306; 403/179; 403/272
[58] Field of Search .............. 174/50.56, 50.61, 50.63, 174/152 GM; 29/631; 128/405, 419 P; 228/120, 122, 124, 179, 180 R, 187, 189, 208, 245, 258, 903; 361/302, 306; 403/28–30, 179, 272

[56] References Cited

U.S. PATENT DOCUMENTS

| | | | |
|---|---|---|---|
| 2,318,435 | 5/1943 | Stupakoff et al. | 174/152 GM |
| 2,431,226 | 11/1947 | Berkey et al. | 174/152 GM X |
| 2,677,781 | 5/1954 | Drieschman | 403/272 X |
| 2,896,008 | 7/1959 | Putz | 174/50.56 |
| 3,063,144 | 11/1962 | Palmour | 174/152 GM X |
| 3,065,533 | 11/1962 | Dungan et al. | 174/152 GM X |
| 3,302,961 | 2/1967 | Franklin | 403/272 |
| 3,710,001 | 1/1973 | Besson | 174/152 GM X |
| 3,853,390 | 12/1974 | DeKoeyer et al. | 174/152 GM X |
| 4,019,080 | 4/1977 | Besson | 228/122 X |
| 4,072,154 | 2/1978 | Anderson et al. | 128/419 P |

FOREIGN PATENT DOCUMENTS

| | | | |
|---|---|---|---|
| 231342 | 1/1964 | Austria | 228/122 |
| 714801 | 12/1941 | Fed. Rep. of Germany | 174/152 GM |
| 596835 | 1/1948 | United Kingdom | 174/152 GM |
| 427398 | 1/1975 | U.S.S.R. | 174/152 GM |

Primary Examiner—Laramie E. Askin
Attorney, Agent, or Firm—Weingarten, Maxham & Schurgin

[57] ABSTRACT

A feedthrough connector for use on an implantable electronic cardiac pacer. A single structure provides a means for connecting a heart lead to the pacer and feedthrough into the body of the pacer. The feedthrough may include filtering means to protect against external interferences. The entire structure has provisions for physical compliance to absorb stresses due to different heat coefficients and as may be caused during assembly and use. Also disclosed is a method for making the feedthrough connector.

15 Claims, 5 Drawing Figures

FEEDTHROUGH CONNECTOR FOR IMPLANTABLE CARDIAC PACER

FIELD OF THE INVENTION

This invention relates generally to implantable heart stimulating devices and more particularly concerns a feedthrough connector for transmitting signals between the heart and the pacer circuitry.

DISCUSSION OF THE PRIOR ART

It is a requirement of implantable cardiac pacers to protect the patient from internal contamination of the body by materials used in the pacer and to protect the materials used in the pacer from detrimental corrosive attack by the body fluids which exist around the pacer. In the current generation of pacers the case or housing for the electronics is normally also the exterior of the pacer. There are several reasons why it has been found advantageous not to encapsulate the entire structure with epoxy, among them being size, longevity and reliability. The external housing will normally be made of stainless steel, titanium or other suitable materials which are substantially inactive in the human body. In such a configuration, the only component of the pacer which is, of necessity, not enclosed within the housing is the heart lead connector. Such connector must be insulated from the housing and must provide connection between the heart lead and the pacer circuitry. In addition it is often desirable to provide protection from external sources of interference, such as radio frequency or electromagnetic radiation.

An example of the known prior art is contained in U.S. Pat. No. 4,010,759 wherein the heart lead couples to a socket embedded in the supporting encapsulant at the header end of the pacer. A feed wire, normally helical in configuration, extends from the socket to a bushing which constitutes the feedthrough into the body of the pacer. Normally an externally accessible screw perpendicular to the axis of the socket is used to secure the heart lead to the socket.

Another example of a feedthrough assembly is shown in U.S. Pat. No. 3,920,888 but this patent does not reveal the entire header assembly for connecting the heart lead to the feedthrough. Some discrete feedthroughs have included a filter to provide protection from external interferences.

The heretofore known prior art involving a separate socket coupled by means of a feed wire to the feedthrough or bushing in the header of the pacer housing had several disadvantages. Some of such disadvantages are the necessity for a castable support system such as epoxy, and the need for connections between the socket, feed wire and feedthrough which are vulnerable to corrosion.

SUMMARY OF THE INVENTION

It is an object of this invention to provide a simplified composite feedthrough connector for coupling the heart lead to the pacer circuitry. Broadly speaking, this invention comprises a ceramic cylinder mounted compliantly to the cover or header of the pacer housing. Mounted compliantly to the ceramic cylinder is a terminal block to which is mounted the stud for connection within the pacer housing to the circuitry therein. The terminal block includes means for securing the heart lead thereto. This entire structure is hermetically self-sealed to protect its elements and the pacer from the body fluids and the body from pacer contamination. The feedthrough connector of this invention eliminates the need for a cast support system and allows the connections to the pacer circuitry to be made within the hermetic enclosure.

BRIEF DESCRIPTION OF THE DRAWING

The objects, advantages and features of this invention will be more clearly understood from the following detailed description when read in conjunction with the accompanying drawing in which.

DESCRIPTION OF THE PREFERRED EMBODIMENTS

Figure 1:
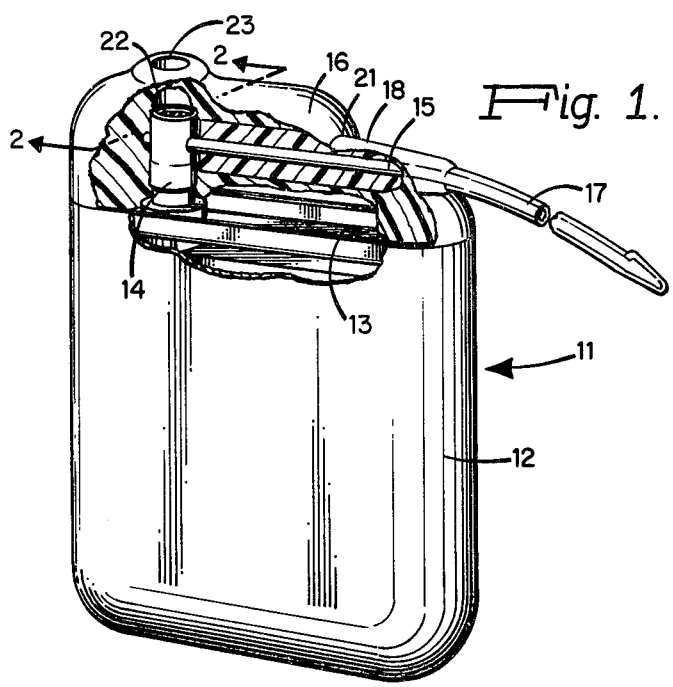
FIG. 1 is a perspective partially broken away view of a pacer including the present invention.

With reference now to the drawing and more particularly to FIG. 1 thereof, there is shown a pacer 11 comprised of a housing 12, a header 13, a feedthrough connector assembly 14 to which is connected heart lead 15. The connector assembly and the end of the heart lead are surrounded by a molded cover 16 which is sealed to the header of the pacer. Wire 15 is closely surrounded throughout its length by an insulative sleeve 17 external of cover 16. Enlarged portion 18 of the sleeve forms a tight fit with respect to opening 21 through which the wire and sleeve pass into the cover to connect with the connector assembly. The wire is secured to connector 14 by means of a screw 22, access to which is provided through opening 23 in the top of cover 16.

Figure 3:
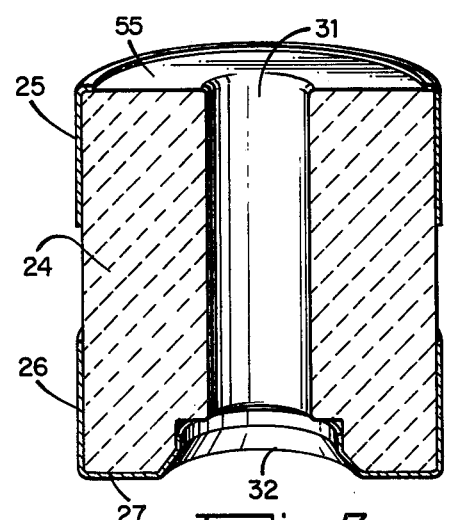
FIG. 3 is a perspective sectional view of the ceramic cylinder shown in FIG. 2.
Figure 2:
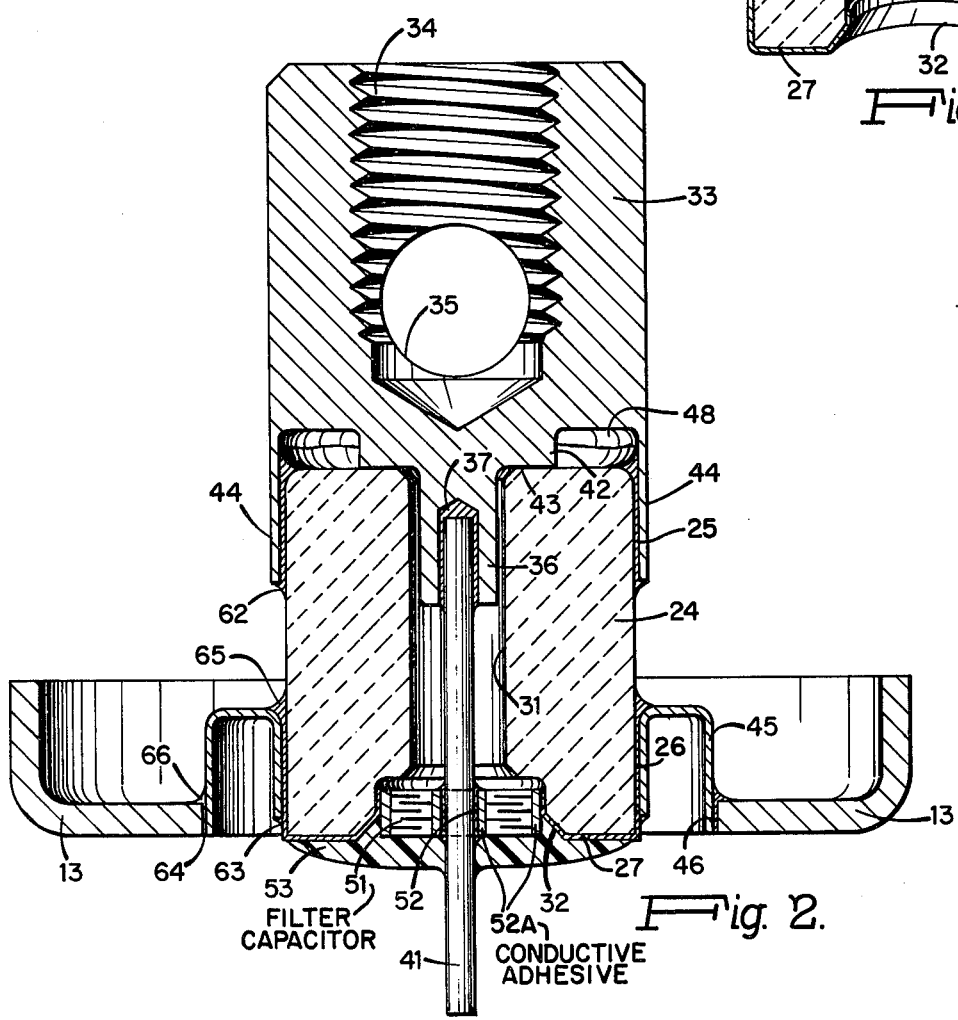
FIG. 2 is an enlarged sectional view taken along cutting plane 2—2 of FIG. 1 showing the feedthrough connector of the invention.

With reference now to FIGS. 2 and 3, the feedthrough connector assembly will be discussed in detail. An electrically insulative cylinder 24 made of a suitable ceramic material such as alumina is metalized on the upper portion of the external cylindrical surface as indicated by reference numeral 25 and on the lower portion of the external cylindrical surface extending around to the underside as indicated by reference numerals 26 and 27. The cylinder is provided with an axial bore 31 through its length and an enlarged chamfered opening 32 at the bottom thereof communicating with the bore. Terminal element 33 is shown as being generally cylindrical in shape and has a blind threaded axial opening 34 in the top portion thereof which is intersected by a diametrical hole 35 extending through the upper portion of the terminal. At the lower end of the terminal there is a cylindrical projection 36 having a blind hole 37 axially formed therein. One end of an electrically conductive wire or stud 41 is secured within hole 37 by a suitable high temperature braze material. Also centrally extending downwardly from the body of terminal 33 is cylindrical projection 42 forming an annular shoulder 43 which is at right angles to and larger than projection 36. Thin cylindrical side wall 44, preferably formed unitarily with terminal 33, extends downwardly from the body of the terminal a distance below shoulder 43 substantially similar to the length of metalization 25 on sleeve 24. Extension 44 could also be a separately formed element which is secured, preferably by welding, to terminal 33. An appropriate notch would be formed at the bottom external surface of the terminal for a short overlap of the thin walled extension. Shoulder 43 extends outwardly from the axis of terminal 33 a distance greater than the radius of bore 31 in cylinder 24 leaving a space 48 between the top of the cylinder and the bottom surface of the terminal. The purpose of this space will be explained hereinbelow. While the terminal element is shown with an external cylindrical configuration, no particular shape is necessary, only that projection 44 must conform closely to the outer surface of cylinder 24. Further, the threaded opening may be horizontal and the hole 35 may be vertical if desired.

An annular base ring 45 having a U-shaped cross section is mounted between the inner diameter of opening 46 in header 13 and ceramic cylinder 24. Wall 44 is secured to metalized surface 25 of cylinder 24 by means of brazing as is base ring 45 secured to metalized area 26 on the cylinder and to header 13. The braze material used for these three junctions preferably melts at a lower temperature than the braze material used for securing stud 41 to terminal 33. A conventional filter capacitor 51 having an axial opening 52 therethrough is fitted over stud 41 into enlarged opening 32 in ceramic cylinder 24 and is secured therein by an appropriate adhesive 52A such as epoxy. Since electrical connection between the exterior of the capacitor and the pacer housing is desired, the adhesive will normally be electrically conductive to couple to header 13 through metalization 27, ring 45 and the intermediate braze areas. The entire end of ceramic cylinder 24 including capacitor 51 is then encapsulated by suitable encapsulant such as epoxy 53 for physical protection prior to final assembly.

Figure 4:
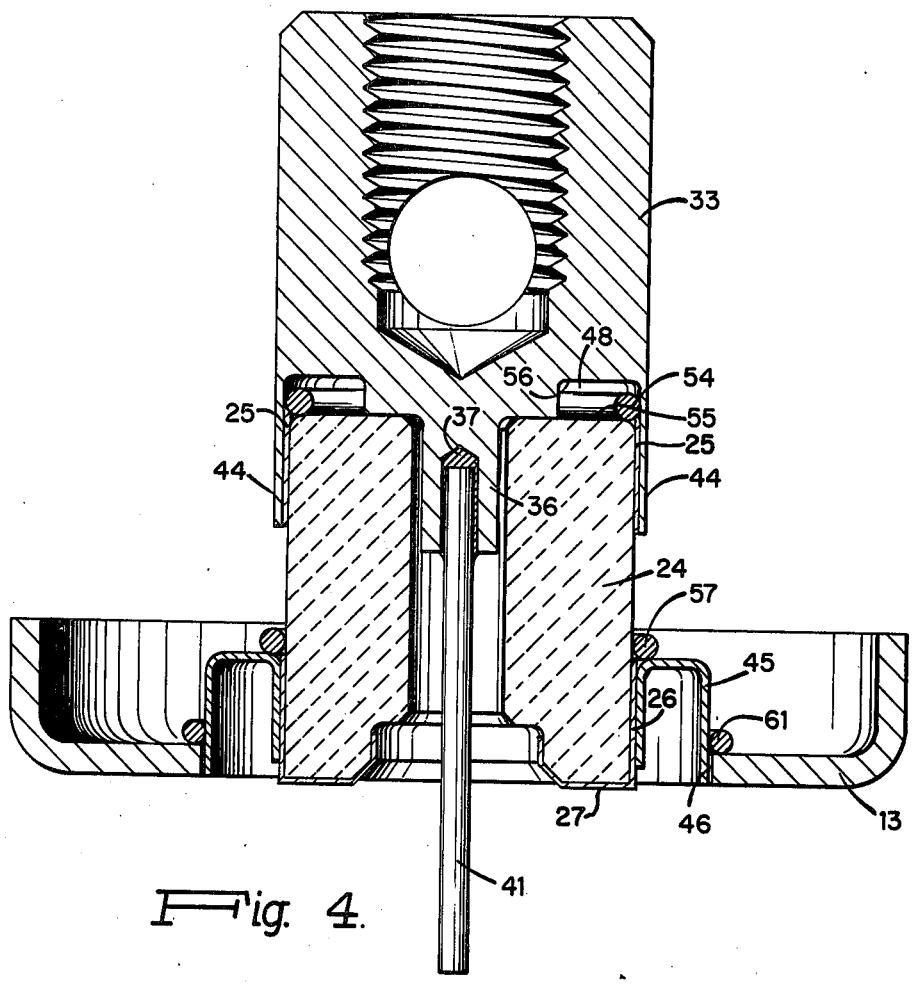
FIG. 4 is a view similar to FIG. 2 showing a step in the process of making the structure of the invention.

With reference now to FIG. 4 the steps involved in making this invention will be described. After stud 41 is secured in hole 37 in projection 36, a ring 54 or other suitable configuration of braze material is placed within the opening defined by thin cylindrical wall 44 of terminal 33, and the terminal is mounted on top of ceramic cylinder 24 thereby placing the braze material in space 48 between the top surface 55 of the ceramic cylinder and annular bottom surface 56 of terminal 33. Thin wall 44 closely confines the metalized upper surface 25 of ceramic cylinder 24. Another ring 57 of similar braze material is placed over the outside diameter of ceramic cylinder 24 and the bottom portion of the cylinder is inserted within base ring 45. This entire assembly is then inserted into opening 46 in header 13 so that the bottom of the outer flange of base ring 45 and the bottom of ceramic cylinder 24 are substantially coplanar with the bottom surface of header 13. A third ring of braze material 61 is located at the junction of base ring 45 and header 13.

This entire assembly, suitably held with the components in their desired relative positions, is then heated to a temperature so that braze materials 54, 57 and 61 soften and flow between the metal or metalized surfaces which are in surface contact or closely adjacent each other. Note that due to normally expected heat coefficients, terminal 33 and consequently wall 44 will tend to expand in diameter more than ceramic cylinder 24, thereby allowing braze material 54 to flow down between wall 44 and metalized surface 25. Similarly, braze materials 57 and 61 will flow between the two metal or metalized surfaces with which they are in respective contact. Because the braze material securing stud 41 in hole 37 melts at a higher temperature than the other braze materials, this joint is unaffected during the heating process. The structure is then cooled, the braze material normally solidifying substantially before the metal of wall 44 returns to its normal size. Thus thin wall 44 will tend to shrink upon an outside diameter of the metalized upper portion of ceramic cylinder 24 which is of greater diameter than it was before the heating step due to the addition of the braze material. In this way thin cylindrical wall 44 will very tightly adhere to and compress upon cylinder 24 but because the wall is so thin, no undue stresses will occur upon the cylinder. The thinness of wall 44 and space 48 provides the necessary compliance at the interface between the terminal and cylinder for a secure attachment of two dissimilar elements without possible damage to the ceramic. A very secure hermetic seal is created between terminal 33 and cylinder 24. Any stresses at the bottom of cylinder 24 which might be created due to thermal expansions and contractions as well as handling and assembly procedures will be absorbed by the compliance offered by base ring 45 which acts as a bellows. Because of the location of braze rings 54, 57 and 61 and the fact that the structure is heated in an upright position, it may be easily inspected to see if proper brazing has occurred by observing the flow of braze material through the entire metal facing surface contacts (see FIG. 2) as indicated by the wicking menisci 62, 63 and 64, the latter two being inspected in conjunction with visible tapered braze fillets 65 and 66 respectively. Note that the braze material flows only as far as the metalized surface on cylinder 24 and that the terminal is electrically insulated from header 13. The flange of ring 45 abutting the cylinder is somewhat shorter than the outer flange, thereby facilitating inspection of braze meniscus 63. One side of the pacer electrical circuit is connected to the outside of capacitor 51 through header 13, ring 45, metalization 26 and 27 and the braze joints. The other size of the circuit is connected through stud 41 and terminal 33 to heart lead 15. The other electrical terminal of the capacitor is connected to stud 41.

When the structure has been completed in accordance with the steps of FIG. 4, it is assembled with the body 12 of the pacer with electrically conducting stud 41 being connected to the electrical circuitry of the pacer and header 13 forming the top of the housing and being secured thereto by a hermetic seal. Finally, cover 16 is applied as shown and sealed over the top of the pacer. When the pacer is implanted, the electrode which is normally already in place is inserted through hole 21 into hole 35 in connector terminal 33 and secured thereto by means of screw 22 through access hole 23.

Figure 5:
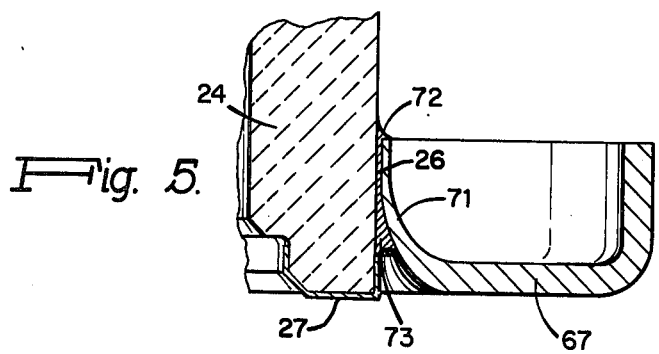
FIG. 5 is a partial view similar to a portion of FIG. 2 showing an alternative means for compliant assembly.

The primary function of ring 45 is to provide compliance between cylinder 24 and header 13. Such compliance can be achieved in other ways, such as using a ring with an S- or J-shaped cross section. Another alternative embodiment is shown in FIG. 5 wherein the metal of header 67 is made somewhat thinner and curved at 71 to intersect the metalized wall of the cylinder. The necessary flexibility is provided, a separate compliant element is eliminated and only one braze joint is necessary with upper fillet 72 and lower meniscus 73 being clearly visible for inspection purposes.

With significant differences in the thermal coefficient of expansion between cylinder 24 and terminal 33, the compliant properties of extension 44 together with space 48 are desirable. By selecting the cylinder and terminal materials to have more closely matched coefficients of thermal expansion, extension 44 need have less compliance, allowing the use of a thicker-walled extension.

An alternative method of assembling the elements is to invert them, placing the braze rings at the points previously identified by reference numerals 62, 63 and 64. The assembly would otherwise be substantially the same as previously described.

In view of the above description, it is likely that modifications and improvements will occur to those skilled in the art which are within the scope of this invention.

What is claimed is:

1. A feedthrough connector for an implantable electronic cardiac pacer mounted within a housing, said connector comprising:
   a header adapted to form the cover of the housing of said pacer, said header having an opening therethrough;
   a compliant ring secured to said header in said opening;
   an electrically insulative cylinder having one end mounted within said ring;
   a terminal block mounted to the other end of said insulative cylinder, the external surface of said terminal block having a thin-walled compliant cylindrical extension closely surrounding said other end of said insulative cylinder, said terminal block having an annular bottom surface within said compliant cylindrical extension spaced from the top of said insulative cylinder to facilitate compliant action between said thin-walled extension and said insulative cylinder, said terminal block being formed with a blind threaded bore opening into one surface thereof, and a hole diametrically intersecting said threaded bore, said hole being adapted to receive an uninsulated end of a heart lead; and
   a screw having threads mating with said threaded bore, said screw being adapted to secure the heart lead in said hole;
   said thin-walled cylindrical extension being brazed and shrunk onto said insulative cylinder, said ring being brazed to said one end of said insulative cylinder.

2. The connector recited in claim 1 wherein said ring has a U-shaped cross section, one flange thereof being secured to said header and the other flange thereof being secured to said insulative cylinder.

3. The connector recited in claim 2 wherein said ring acts as a bellows between said insulative cylinder and said header thereby providing compliance to account for thermal and mechanical stresses resulting from brazing and assembly of said connector to said pacer.

4. The connector recited in claim 1 wherein said insulative cylinder is made of a ceramic.

5. The connector recited in claim 1 wherein said insulative cylinder is formed with an axial hole therethrough.

6. The connector recited in claim 5 wherein said insulative cylinder is further formed with an enlarged axial opening at said one end, said opening being adapted to receive a filter capacitor.

7. The connector recited in claim 6 wherein:
   said terminal block is formed with an axial projection surrounded by and spaced from said thin-walled extension, said projection having an axial hole bored therein;
   said connector further comprises an electrically conductive stud having one end secured in said axial hole in said projection, said projection extending into said axial hole in said insulative cylinder and said stud extending through said axial hole and beyond said one end of said insulative cylinder.

8. The connector recited in claim 7 and further comprising a cylindrical filter capacitor having an axial hole therethrough, said stud extending through said hole in said capacitor, said capacitor being secured in said enlarged axial opening in said insulative cylinder.

9. The connector recited in claim 8 wherein the external cylindrical surface of said insulative cylinder adjacent said one end and adjacent said other end are metalized, said cylindrical metalized surface areas being electrically and physically separate, said one end of said insulative cylinder being metalized to facilitate electrical connection between said one end and said header through said ring.

10. The connector recited in claim 9 wherein said terminal and said stud provide one external electrical connection to one terminal of said capacitor, said stud is adapted to provide electrical connection to pacer circuitry, and said header provides the other external electrical connection in conjunction with said housing, said header being electrically connected to the other terminal of said capacitor through said ring.

11. The connector recited in claim 1 wherein said insulative cylinder is formed with an axial hole therethrough and an enlarged axial opening at said one end, the external cylindrical surface of said insulative cylinder adjacent said one end and adjacent said other end is metalized, said cylindrical metalized surface areas being electrically and physically separate, said metalization on said one end of said insulative cylinder extending across the end surface thereof and up into said enlarged axial opening, said connector further comprising:
   an electrically conductive stud having one end secured to said terminal block and extending through said axial hole in said insulative cylinder and beyond said one end thereof;
   a cylindrical filter capacitor having an axial hole therethrough secured in said enlarged axial opening in said insulative cylinder, said stud extending through said hole in said capacitor, one set of electrodes of said capacitor being connected to said header through said metalization on said one end of said insulative cylinder and said compliant ring, the other set of electrodes of said capacitor being connected to said terminal block through said stud which is electrically and physically connected in said axial hole in said capacitor, said stud being adapted to provide electrical connection between a heart lead and pacer circuitry mounted within said housing.

12. A method for forming a feedthrough connector for an implantable electronic cardiac pacer mounted within a housing, said method comprising the steps of:
   metalizing a first cylindrical surface adjacent one end of an insulative cylinder;
   placing a terminal block on top of said one end of said insulative cylinder, said terminal block having a thin-walled cylindrical extension closely surrounding said first metalized surface of said insulative cylinder;
   placing a first ring of braze material in contact with said first metalized surface and with said cylindrical extension;
   heating the assembly thus formed to melt said braze material and expand said cylindrical extension, said braze material flowing between said cylindrical extension and said first metalized surface, thereby effectively enlarging the diameter of said metalized surface; and then cooling said assembly, said braze material solidifying before said cylindrical extension thermally contracts to its normal size, whereby said cylindrical extension contracts upon a surface of greater diameter than the initial metalized cylindrical surface, forming a shrink fit and thereby closely confining said one end of said insulative cylinder within said thin-walled cylindrical extension.

13. The method recited in claim 12 and comprising the further steps of:

metalizing a second cylindrical surface adjacent the other end of said insulative cylinder;

inserting said metalized other end into a compliant base ring connected to a header; and placing a second ring of braze material on the intersection of said second cylindrical surface and said base ring;

said first and second rings of braze material being heated and caused to flow during said heating step and solidifying during said cooling step to thereby form said connector.

14. A feedthrough connector for an implantable electronic cardiac pacer mounted within a housing, said connector comprising:

a header adapted to form the cover of the housing of said pacer, said header having an opening therethrough;

a compliant ring secured to said header in said opening:

an electrically insulative cylinder having one end mounted within said ring, the base surfaces of said header, said ring and said cylinder lying in a common plane;

a terminal block mounted to the other end of said insulative cylinder, the external surface of said terminal block having a thin-walled compliant cylindrical extension closely surrounding said other end of said insulative cylinder, an annular portion of the bottom of said terminal block within said cylindrical extension being spaced from the top of said insulative cylinder to facilitate compliant action between said thin-walled extension and said insulative cylinder, said terminal block being formed with a blind threaded bore opening into one surface thereof, and a diametrical hole intersecting said threaded bore, said diametrical hole being adapted to receive an uninsulated end of a heart lead; and a screw having threads mating with said threaded bore, said screw being adapted to secure said heart lead in said diametrical hole;

said thin-walled cylindrical extension being brazed and shrunk onto said insulative cylinder, said ring being brazed to said one end of said insulative cylinder.

15. The connector recited in claim 14 wherein said insulative cylinder is formed with an axial hole therethrough and is further formed with an enlarged axial opening at said one end, the external cylindrical surface of said insulative cylinder adjacent said one end and adjacent said other end are metalized, said cylindrical metalized surface areas being electrically and physically separate, said metalization on said one end of said insulative cylinder extending across the end surface thereof and up into said enlarged axial opening, said connector further comprising:

an electrically conductive stud having one end secured to said terminal block and extending through said axial hole in said insulative cylinder and beyond said one end thereof;

a cylindrical filter capacitor having an axial hole therethrough secured in said enlarged axial opening in said insulative cylinder, said stud extending through said hole in said capacitor, one set of electrodes of said capacitor being connected to said header through said metalization on said one end of said insulative cylinder and said compliant ring, the other set of electrodes of said capacitor being connected to said terminal block through said stud which is electrically and physically connected in said axial hole in said capacitor, said stud being adapted to provide electrical connection between a heart lead and pacer circuitry mounted within said housing.

* * * * *